(12) United States Patent
Rosendahl

(10) Patent No.: US 6,606,907 B1
(45) Date of Patent: Aug. 19, 2003

(54) MEASUREMENT APPARATUS AND METHOD

(75) Inventor: Glenn Rosendahl, 124 Burrinjuck Crescent, Duffy ACT 2611 (AU)

(73) Assignee: Glenn Rosendahl, Duffy (AU)

( * ) Notice: Subject to any disclaimer, the term of this patent is extended or adjusted under 35 U.S.C. 154(b) by 0 days.

(21) Appl. No.: 09/527,954

(22) Filed: Mar. 16, 2000

Related U.S. Application Data

(63) Continuation-in-part of application No. PCT/AU98/00747, filed on Sep. 11, 1998.

(30) Foreign Application Priority Data

Sep. 12, 1997 (AU) ............................................. PO 9177

(51) Int. Cl.[7] ................................................ G01L 5/00
(52) U.S. Cl. ..................................... 73/379.01; 128/774
(58) Field of Search ........................ 73/379.01–379.04; 128/672, 774; 604/64, 75, 99.02; 482/4, 44, 49

(56) References Cited

U.S. PATENT DOCUMENTS

| | | | |
|---|---|---|---|
| 3,898,983 A | 8/1975 | Elam ............................... | 128/2 |
| 4,050,449 A | 9/1977 | Castellana et al. ............... | 128/2 |
| 4,231,255 A * | 11/1980 | Haski et al. ..................... | 73/379 |
| 4,592,371 A | 6/1986 | Pellicano et al. ............... | 128/774 |
| 4,609,190 A | 9/1986 | Brentham ....................... | 272/130 |
| 4,681,316 A | 7/1987 | DeCloux ......................... | 272/130 |
| 4,949,729 A * | 8/1990 | Haski ............................. | 128/774 |
| 5,119,831 A | 6/1992 | Robin et al. .................... | 128/774 |
| 5,452,727 A | 9/1995 | Tura et al. ...................... | 128/777 |
| 5,643,138 A * | 7/1997 | Huang ............................. | 482/4 |
| 5,643,157 A | 7/1997 | Seliber ........................... | 482/112 |

FOREIGN PATENT DOCUMENTS

| | | |
|---|---|---|
| AU | A-48889/93 | 1/1995 |
| DE | 1 532 360 | 11/1978 |
| EP | 0 244 933 | 3/1987 |
| WO | WO 86/00024 | 1/1986 |

OTHER PUBLICATIONS

D.G. Palmer et al., "Meek Grip Analyser," *Med. & Biol. Eng. & Comput.*, Nov. 1982, 20, pp. 772–774.

* cited by examiner

Primary Examiner—Hezron Williams
Assistant Examiner—Jewel V. Thompson
(74) Attorney, Agent, or Firm—Pillsbury Winthrop LLP

(57) ABSTRACT

An apparatus for assessing the strength of a user is disclosed which includes
  pneumatic reservoir means adapted to be repeatedly vented by the user, and
  measuring means for measuring parameters indicative of strength, work, work rate and speed of muscle contraction of the user in evacuating the reservoir means.

32 Claims, 12 Drawing Sheets

| | A | B | C | D | E | F | G | H | I | J | K | L | M | N |
|---|---|---|---|---|---|---|---|---|---|---|---|---|---|---|
| 1 | CHART 2: "EARLY DETERIORATION". TABULATION AND CALCULATION OF ROSENDAHL PNEUMATIC DYNANOMETER RESULTS | | | | | | | | | | | | | |
| 2 | | | | | | | | | | | | | | |
| 3 | CYCLE | START PUMP PHASE | | START RECOVERY PHASE | | DURATION PUMP PHASE | DURATION RECOVERY PHASE | DURATION COMPLETE CYCLE | | AVERAGE PRESSURE | PRESSURE DIFFERENCE | EQUIVALENT VOLUME | WORK DONE | RATE OF DOING WORK |
| 4 | NUMBER | TIME (SEC) | PRESSURE (mmHg) | TIME (SEC) | PRESSURE (mmHg) | | | | | (mmHg) | (mmHg) | (REV/ml) | (RWU) | (RPU) |
| 5 | | | | | | (-------HUNDREDTHS OF A SECOND-------) | | | | | | | | |
| 6 | | | | | | | | | | | | | | |
| 7 | | | | | | | | | | | | | | |
| 8 | | | | | | | | | | | | | | |
| 9 | | | | | | THE FORMULAE FOR ROW 14 | | | | | | | | |
| 10 | | DATA | DATA | DATA | DATA | =100*(D14-B14) | =100*(b15-b14) | =100*(b15-b14) | | =(c14-e14)/2 | =e114-c14 | =2*j14 | =i14*k14 | =100*l14/h14 |
| 11 | | | | | | | | | | | | | | |
| 12 | | | | | | | | | | | | | | |
| 13 | PARAMETERS GRAPHED: | | | | | GRAPHED | GRAPHED | | X-COORDINATE | | | GRAPHED | GRAPHED | GRAPHED |
| 14 | 1 | 1.56 | 2 | 1.66 | 10 | 10 | 30 | 40 | | 6.0 | 8.0 | 16.0 | 96 | 240 |
| 15 | 2 | 1.96 | 10 | 2.04 | 18 | 8 | 26 | 34 | | 14.0 | 8.0 | 16.0 | 224 | 659 |
| 16 | 3 | 2.30 | 18 | 2.40 | 26 | 10 | 28 | 38 | | 22.0 | 8.0 | 16.0 | 352 | 926 |
| 17 | 4 | 2.68 | 26 | 2.80 | 34 | 12 | 28 | 40 | | 30.0 | 8.0 | 16.0 | 480 | 1200 |
| 18 | 5 | 3.08 | 34 | 3.20 | 42 | 12 | 26 | 38 | | 38.0 | 8.0 | 16.0 | 608 | 1600 |
| 19 | 6 | 3.46 | 42 | 3.56 | 49 | 10 | 30 | 40 | | 45.5 | 7.0 | 14.0 | 637 | 1593 |
| 20 | 7 | 3.86 | 49 | 3.94 | 57 | 8 | 28 | 36 | | 53.0 | 8.0 | 16.0 | 848 | 2356 |
| 21 | 8 | 4.22 | 57 | 4.32 | 65 | 10 | 28 | 38 | | 61.0 | 8.0 | 16.0 | 976 | 2568 |
| 22 | 9 | 4.60 | 65 | 4.70 | 73 | 10 | 28 | 38 | | 69.0 | 8.0 | 16.0 | 1104 | 2905 |
| 23 | 10 | 4.98 | 73 | 5.10 | 80 | 12 | 26 | 38 | | 76.5 | 7.5 | 14.0 | 1071 | 2818 |
| 24 | 11 | 5.36 | 80 | 5.48 | 88 | 12 | 24 | 36 | | 84.0 | 8.0 | 16.0 | 1344 | 3733 |
| 25 | 12 | 5.72 | 88 | 5.86 | 94 | 14 | 30 | 44 | | 91.0 | 6.0 | 12.0 | 1092 | 2482 |
| 26 | 13 | 6.16 | 94 | 6.28 | 101 | 12 | 22 | 34 | | 97.5 | 7.5 | 14.0 | 1365 | 4015 |
| 27 | 14 | 6.50 | 101 | 6.62 | 108 | 12 | 26 | 38 | | 104.5 | 7.0 | 14.0 | 1463 | 3850 |
| 28 | 15 | 6.88 | 108 | 7.00 | 115 | 12 | 26 | 38 | | 111.5 | 7.0 | 14.0 | 1561 | 4108 |

*FIG. 7A*

| A | B | C | D | E | F | G | H | I | J | K | L | M | N |
|---|---|---|---|---|---|---|---|---|---|---|---|---|---|
| 29 | 16 | 7.26 | 115 | 121 | 7.38 | 12 | 24 | 36 | 118.0 | 6.0 | 12.0 | 1416 | 3933 |
| 30 | 17 | 7.62 | 121 | 128 | 7.74 | 12 | 28 | 40 | 124.5 | 7.0 | 14.0 | 1743 | 4358 |
| 31 | 18 | 8.02 | 128 | 134 | 8.12 | 10 | 32 | 42 | 131.0 | 6.0 | 12.0 | 1572 | 3743 |
| 32 | 19 | 8.44 | 134 | 139 | 8.52 | 8 | 26 | 34 | 136.5 | 5.0 | 10.0 | 1365 | 4015 |
| 33 | 20 | 8.78 | 139 | 144 | 8.88 | 10 | 30 | 40 | 141.5 | 5.0 | 10.0 | 1415 | 3538 |
| 34 | 21 | 9.18 | 144 | 149 | 9.26 | 8 | 30 | 38 | 146.5 | 5.0 | 10.0 | 1465 | 3855 |
| 35 | 22 | 9.56 | 149 | 154 | 9.66 | 10 | 28 | 38 | 151.5 | 5.0 | 10.0 | 1515 | 3987 |
| 36 | 23 | 9.94 | 154 | 158 | 10.02 | 8 | 28 | 36 | 156.0 | 4.0 | 8.0 | 1248 | 3467 |
| 37 | 24 | 10.30 | 158 | 163 | 10.40 | 10 | 26 | 36 | 160.5 | 5.0 | 10.0 | 1605 | 4458 |
| 38 | 25 | 10.66 | 163 | 167 | 10.80 | 14 | 28 | 42 | 165.0 | 4.0 | 8.0 | 1320 | 3143 |
| 39 | 26 | 11.08 | 167 | 171 | 11.18 | 10 | 30 | 40 | 169.0 | 5.0 | 10.0 | 1352 | 3380 |
| 40 | 27 | 11.48 | 171 | 176 | 11.60 | 12 | 26 | 38 | 173.5 | 5.0 | 10.0 | 1735 | 4566 |
| 41 | 28 | 11.86 | 176 | 180 | 11.94 | 8 | 26 | 34 | 178.0 | 4.0 | 8.0 | 1424 | 4188 |
| 42 | 29 | 12.20 | 180 | 184 | 12.32 | 12 | 26 | 38 | 182.0 | 4.0 | 8.0 | 1456 | 3832 |
| 43 | 30 | 12.58 | 184 | 188 | 12.68 | 10 | 28 | 38 | 186.0 | 4.0 | 8.0 | 1488 | 3916 |
| 44 | 31 | 12.96 | 188 | 191 | 13.06 | 10 | 26 | 36 | 189.5 | 3.0 | 6.0 | 1137 | 2992 |
| 45 | 32 | 13.34 | 191 | 194 | 13.44 | 10 | 28 | 38 | 192.5 | 3.0 | 6.0 | 1155 | 3208 |
| 46 | 33 | 13.70 | 194 | 198 | 13.82 | 12 | 26 | 38 | 196.0 | 4.0 | 8.0 | 1568 | 4126 |
| 47 | 34 | 14.08 | 198 | 202 | 14.22 | 14 | 26 | 40 | 200.0 | 4.0 | 8.0 | 1600 | 4000 |
| 48 | 35 | 14.48 | 202 | 205 | 14.62 | 14 | 24 | 38 | 203.5 | 3.0 | 6.0 | 1221 | 3213 |
| 49 | 36 | 14.86 | 205 | 208 | 15.02 | 16 | 24 | 40 | 206.5 | 3.0 | 6.0 | 1239 | 3098 |
| 50 | 37 | 15.26 | 208 | 212 | 15.38 | 12 | 28 | 40 | 210.0 | 4.0 | 8.0 | 1680 | 4200 |
| 51 | 38 | 15.66 | 212 | 216 | 15.74 | 8 | 28 | 36 | 214.0 | 4.0 | 8.0 | 1712 | 4756 |
| 52 | 39 | 16.02 | 216 | 219 | 16.12 | 10 | 28 | 38 | 217.5 | 3.0 | 6.0 | 1305 | 3434 |
| 53 | 40 | 16.40 | 219 | 222 | 16.50 | 10 | 26 | 36 | 220.5 | 3.0 | 6.0 | 1323 | 3675 |
| 54 | 41 | 16.76 | 222 | 225 | 16.86 | 10 | 28 | 38 | 223.5 | 3.0 | 6.0 | 1341 | 3529 |
| 55 | 42 | 17.14 | 225 | 228 | 17.26 | 12 | 28 | 40 | 226.5 | 3.0 | 6.0 | 1359 | 3398 |

*FIG. 7B*

| | A | B | C | D | E | F | G | H | I | J | K | L | M | N |
|---|---|---|---|---|---|---|---|---|---|---|---|---|---|---|
| 56 | 43 | 17.54 | 228 | 17.64 | 231 | 10 | 28 | 38 | 229.5 | 3.0 | 6.0 | 1377 | 3624 | |
| 57 | 44 | 17.92 | 231 | 18.00 | 234 | 8 | 30 | 38 | 232.5 | 3.0 | 6.0 | 1395 | 3671 | |
| 58 | 45 | 18.30 | 234 | 18.40 | 236 | 10 | 30 | 40 | 235.0 | 2.0 | 4.0 | 940 | 2350 | |
| 59 | 46 | 18.70 | 236 | 18.78 | 239 | 8 | 28 | 36 | 237.5 | 3.0 | 6.0 | 1425 | 3958 | |
| 60 | 47 | 19.06 | 239 | 19.14 | 242 | 8 | 30 | 38 | 240.5 | 3.0 | 6.0 | 1443 | 3797 | |
| 61 | 48 | 19.44 | 242 | 19.54 | 245 | 10 | 26 | 36 | 243.5 | 3.0 | 6.0 | 1461 | 4058 | |
| 62 | 49 | 19.80 | 245 | 19.92 | 248 | 12 | 28 | 40 | 246.5 | 3.0 | 6.0 | 1479 | 3698 | |
| 63 | 50 | 20.20 | 248 | 20.30 | 251 | 10 | 26 | 36 | 249.5 | 3.0 | 6.0 | 1497 | 4158 | |
| 64 | 51 | 20.56 | 251 | 20.66 | 254 | 10 | 30 | 40 | 252.5 | 3.0 | 6.0 | 1515 | 3787 | |
| 65 | 52 | 20.96 | 254 | 21.04 | 257 | 8 | 28 | 36 | 255.5 | 3.0 | 6.0 | 1533 | 4258 | |
| 66 | 53 | 21.32 | 257 | 21.44 | 259 | 12 | 26 | 38 | 258.0 | 2.0 | 4.0 | 1032 | 2716 | |
| 67 | 54 | 21.70 | 259 | 21.82 | 262 | 12 | 26 | 38 | 260.5 | 3.0 | 6.0 | 1563 | 4113 | |
| 68 | 55 | 22.08 | 262 | 22.18 | 265 | 10 | 28 | 38 | 263.5 | 3.0 | 6.0 | 1581 | 4161 | |
| 69 | 56 | 22.46 | 265 | 22.58 | 268 | 12 | 28 | 40 | 266.5 | 3.0 | 6.0 | 1599 | 3997 | |
| 70 | 57 | 22.86 | 268 | 22.98 | 271 | 12 | 26 | 38 | 269.5 | 3.0 | 6.0 | 1617 | 4255 | |
| 71 | 58 | 23.24 | 271 | 23.34 | 274 | 10 | 28 | 38 | 272.5 | 3.0 | 6.0 | 1635 | 4303 | |
| 72 | 59 | 23.62 | 274 | 23.70 | 277 | 8 | 28 | 36 | 275.5 | 3.0 | 6.0 | 1653 | 4592 | |
| 73 | 60 | 23.98 | 277 | 24.08 | 279 | 10 | 30 | 40 | 278.0 | 2.0 | 4.0 | 1112 | 2780 | |
| 74 | 61 | 24.38 | 279 | 24.46 | 282 | 10 | 28 | 38 | 280.5 | 3.0 | 6.0 | 1683 | 4429 | |
| 75 | 62 | 24.76 | 282 | 24.86 | 285 | 10 | 28 | 38 | 283.5 | 3.0 | 6.0 | 1701 | 4476 | |
| 76 | 63 | 25.14 | 285 | 25.24 | 288 | 10 | 24 | 34 | 286.5 | 3.0 | 6.0 | 1719 | 5056 | |
| 77 | 64 | 25.48 | 288 | 25.60 | 291 | 12 | 28 | 40 | 289.5 | 3.0 | 6.0 | 1737 | 4343 | |
| 78 | 65 | 25.88 | 291 | 26.00 | 294 | 12 | 28 | 40 | 292.5 | 3.0 | 6.0 | 1755 | 4387 | |
| 79 | 66 | 26.28 | 294 | 26.36 | 297 | 8 | 28 | 36 | 295.5 | 3.0 | 6.0 | 1773 | 4925 | |
| 80 | 67 | 26.64 | 297 | 26.74 | 300 | 10 | 28 | 38 | 298.5 | 3.0 | 6.0 | 1791 | 4713 | |
| 81 | 68 | 27.02 | 300 | 27.12 | | | | | | | | | | |
| 82 | | | | | | | | | | | | | | |

*FIG. 7C*

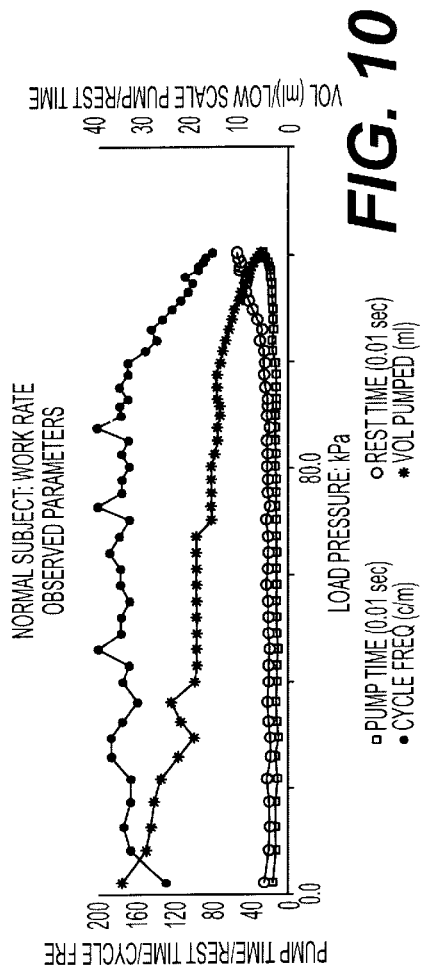
FIG. 10
FIG. 9
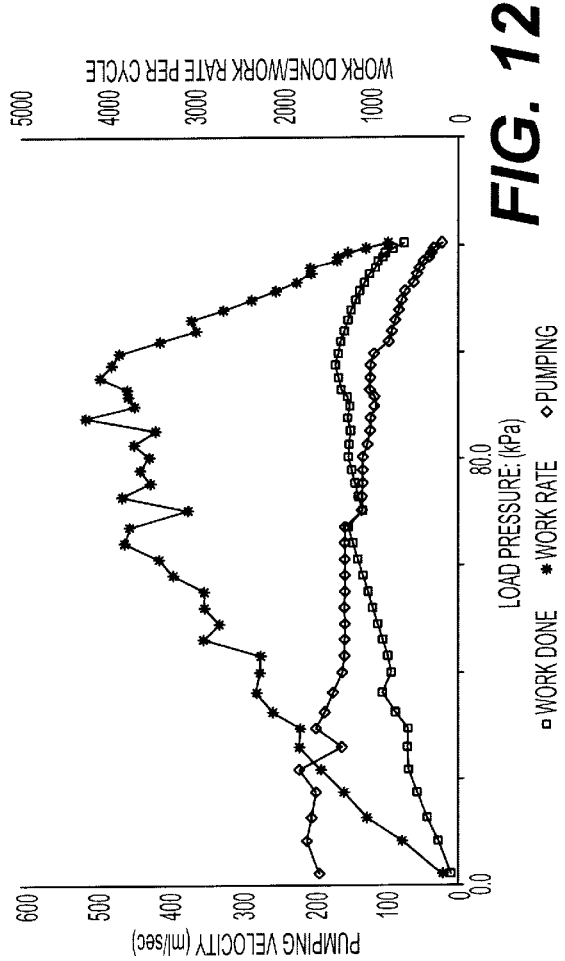
FIG. 12
FIG. 11

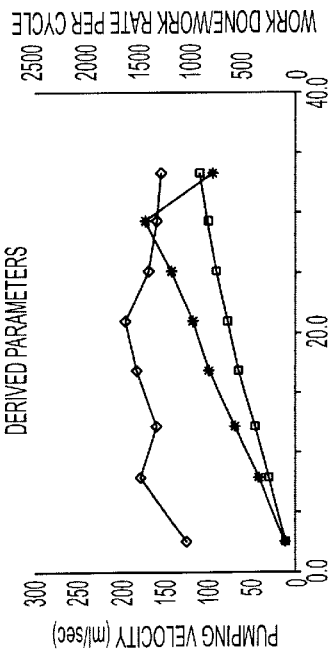
FIG. 24
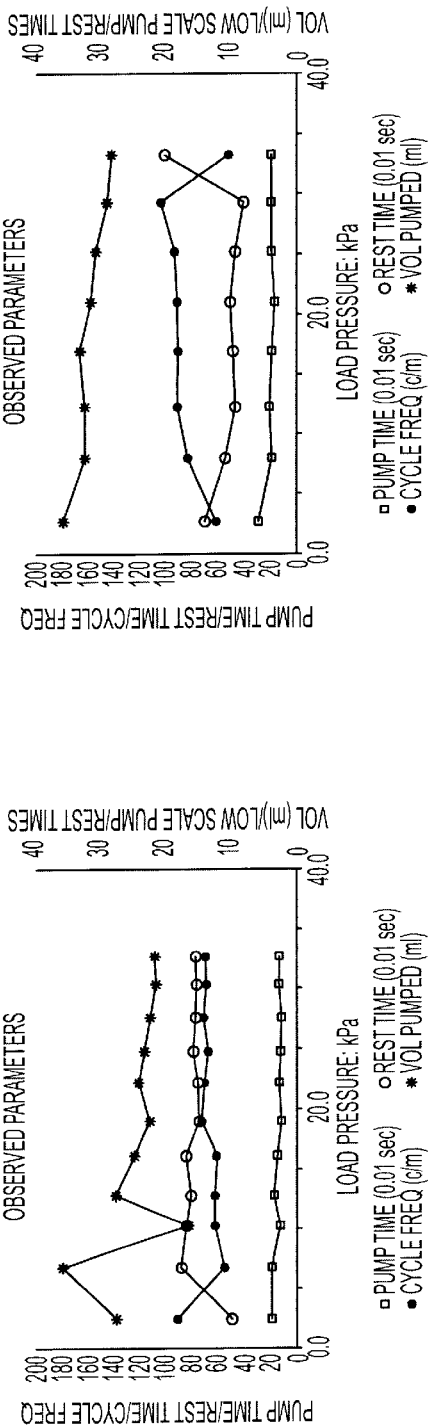
FIG. 23
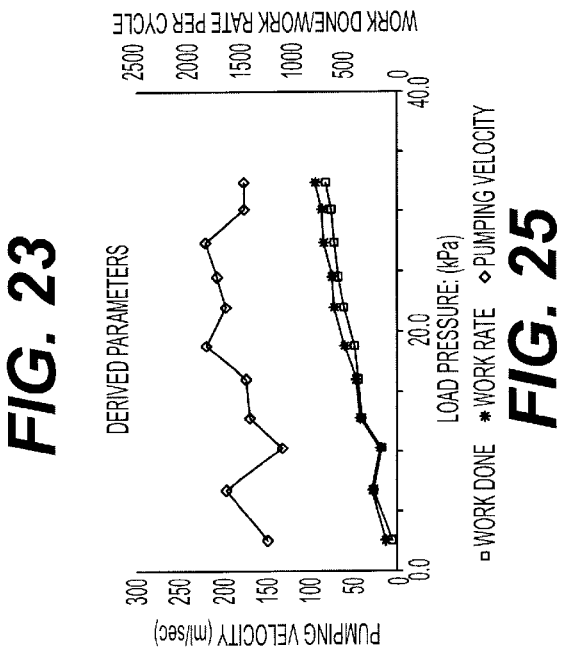
FIG. 26
FIG. 25

MEASUREMENT APPARATUS AND METHOD

This is a Continuation-in-Part of International Appln. No. PCT/AU98/00747 filed Sep. 11, 1998.

TECHNICAL FIELD

This invention relates to a measurement apparatus and method.

This invention relates particularly to an apparatus and method for assessing the strength of a user. The invention has particular application to an apparatus and method for measuring the strength, work capacity, work rate and speed of muscle contraction of the human hand although it will be appreciated that the invention may be used to measure non-human strength and work capacity and to measure the strength and work capacity of humans other than that generated by the hand.

The invention has particular application to apparatus and methods for measuring the strength, work rate and speed of muscle contraction of the hand of a person with hand disability, including occupational overuse syndrome which is also known as cumulative trauma disorder or repetition strain injury (RSI).

BACKGROUND OF INVENTION

Grip strength dynamometers for measuring the strength of the hand to perform grasping work, including persons with RSI, are known. Known devices have a pair of substantially parallel spaced apart bars which are drawn together by hand against a fixed force with the strength of the grip being measured. Such apparatus is essentially a modified strain meter which quantitatively assesses the strength of the isometric grasp of the hand.

SUMMARY OF INVENTION

The present invention aims to provide an alternative to known apparatus of the above type.

This invention in one aspect resides broadly in an apparatus for assessing the strength of a user, the apparatus including:

pneumatic reservoir means adapted to be repeatedly vented by the user by deformation thereof;

measuring means for measuring parameters indicative of at least one of strength, work, work rate and speed of muscle contraction of the user associated with evacuation of the reservoir means, and display means for displaying the indicative parameters thus measured.

As used herein the expressions "vent" and "evacuate" and derivatives thereof are substantially synonomous. The expressions refer to causing the reservoir means to be at least partially emptied of the gas or fluid therein.

In a preferred embodiment the pneumatic reservoir means is deformable.

In another aspect this invention resides broadly in a method of comparatively assessing the strength of a user, the method including:

causing the user to repeatedly vent a pneumatic reservoir;

measuring parameters indicative of at least one of strength, work, work rate and speed of muscle contraction of the user in repeatedly evacuating the pneumatic reservoir, and displaying indications of strength, work, work rate and speed of muscle contraction thus measured in comparison with a norm.

The pneumatic reservoir means may be any suitable means adapted to be repeatedly vented and could for example be a bellows, such as an organ-type bellows, which can be repeatedly vented by a user's foot or arm action. Alternatively the pneumatic reservoir means may be a piston and cylinder arrangement in which either may be actuated by a lever mechanism.

In one preferred embodiment the pneumatic reservoir means is a resilient bladder adapted to resile from a deflated configuration after evacuation to an inflated configuration for re-evacuation.

Alternatively the pneumatic reservoir means may be a limp collapsible bladder, the apparatus including a source of positive pressure to re-inflate the limp bladder from a deflated configuration after evacuation to an inflated configuration for re-evacuation.

In one arrangement the apparatus includes a constant volume chamber pneumatically connected to the pneumatic reservoir means and the measuring means includes pressure measuring means to measure the pressure in the constant volume chamber.

In a second arrangement the apparatus includes a valve operable at a predetermined pressure, ie a constant pressure valve, and pneumatically connected to the pneumatic reservoir means to thereby define the pressure to be exceeded before the pneumatic reservoir means can be vented, and the measuring means includes volume measuring means for measuring the volume of air expelled from the constant pressure valve.

It is to be understood for this arrangement to work, the volume of the pneumatic pipe linking the exit valve of the pneumatic reservoir, the pressure measuring means and the constant pressure valve, ie the high pressure line, is trivial in relation of the volume of gas usually expelled from the pneumatic reservoir. Thus each hand pump action results in sufficient pressure in the pneumatic reservoir and the high pressure line to open the constant pressure valve and eject a significant volume of gas, approximating the volume of gas ejected from the pneumatic reservoir.

In a variation of this arrangement, a constant volume chamber can be connected to the high pressure line. In this case, as the pneumatic reservoir is repetitively emptied, the pressure of the gas in the constant volume chamber will increase until it reaches the pressure setting of the constant pressure valve. From this event, further repetitive evacuation of the pneumatic reservoir will result in gas being released by the constant pressure valve at its pressure setting with no further increments of pressure occurring in any part of the high pressure line, including the constant volume chamber.

In both arrangements the volume of the constant volume chamber may be selectively variable. The operating pressure of the constant pressure valve may also be selectively variable with the measuring means including pressure measuring means to measure the pressure at which the constant pressure valve operates.

It is preferred that the measuring means includes time measuring means for measuring the time at the beginning and end of each evacuation and calculating means for calculating the time taken to actively deflate the pneumatic reservoir means (pump duration) and the time before initiation of the next pump cycle (recovery duration). The measuring means may also include calculating means for calculating parameters indicative of strength, work, work rate and speed of muscle contraction of the user.

In one embodiment of the invention the constant volume chamber is connected with a variable bleed valve (as opposed to a constant pressure valve) to selectively vary the pressure in the constant volume chamber such that the pressure therein remains substantially constant after each successive evacuation thereof. The rate of bleeding through the bleed valve is proportional to the setting of the valve and to the pressure in the chamber. By continually bleeding air from the chamber, and with a constant pumping rate, and constant volume of evacuation of the pressure reservoir, the pressure in the constant volume chamber remains substantially constant after each successive evacuation.

The measuring means may include pressure measuring means to measure the pressure at which a constant pressure valve operates, and control means to control the pressure at which a constant pressure valve operates or to vary the setting of the variable bleed valve. The control means thus control the pressure level of a constant pressure valve or the proportion of air bled from a variable bleed valve.

The apparatus may also include control means for controlling the volume of the constant volume chamber, and/or control means for controlling the initial pressure of the constant volume chamber, and/or control means for controlling the pressure of a positive pressure source for supply to a limp collapsible bladder.

The apparatus preferably includes pressure generating means operable by an analyst to selectively control the initial pressure in the constant volume chamber.

It is preferred that the apparatus includes non-return valve means located at the inlet and outlet of the pneumatic reservoir means, the non-return valve means respectively preventing reflux of a gas from the pneumatic reservoir when operated by a user and preventing reflux of gas from the constant volume chamber to the reservoir after operation of the reservoir by the user.

The apparatus may also include time indicating means such as a metronome for indicating time intervals to a user. The time intervals may be the desired time of muscle contraction.

The parameters indicative of strength, work, work rate and speed of muscle contraction of the user preferably include one or more of the following specific parameters:

a. contraction or pump duration
b. rest or recovery duration
c. total cycle time (which conveniently can be presented as the inverse, ie "cycle frequency"), this being equivalent to the metronome rate of this cycle
d. volume of gas vented (stated in volumetric or "volume equivalent pressure" terms)
e. cycle load or pressure overcome (the average pressure in the fixed volume chamber for the cycle, or the pressure set in the pressure release valve, if that component is functioning)
f. work performed
g. power achieved
h. volumetric muscle shortening velocity (this is a general measure of the average shortening velocity of the contracting muscles acting on the pneumatic reservoir, stated as the volumetric rate of air venting (per unit time) from the pneumatic reservoir).

The assessment method has been found to produce beneficial physiological and psychological effects and accordingly in a further aspect this invention resides broadly in a method of treatment of patients having muscle weakness, the method including:

causing the patient to repeatedly vent a pneumatic reservoir;

measuring parameters indicative of at least one of strength, work, work rate and speed of muscle contraction of the patient in repeatedly evacuating the pneumatic reservoir, and displaying to the patient indications of strength, work, work rate and speed of muscle contraction thus measured in comparison with previous patient's indications;

whereby the action of repeated evacuation has a beneficial physiological effect for the patient and the display of improved indications in comparison with previous indications has a beneficial psychological effect for the patient.

In another aspect this invention resides broadly in a method of monitoring the state of weakness and clinical improvement of a patient having muscle weakness, the method including:

causing the patient to repeatedly vent a pneumatic reservoir;

measuring parameters indicative of at least one of strength, work, work rate and speed of muscle contraction of the patient in repeatedly evacuating the pneumatic reservoir, and displaying indications of strength, work, work rate and speed of muscle contraction thus measured in comparison with a norm.

DESCRIPTION OF DRAWINGS

In order that this invention may be more easily understood and put into practical effect, reference will now be made to the accompanying drawings which illustrate a preferred embodiment of the invention, wherein:

FIGS. 7A–7C are a tabulation produced in accordance with the invention, and

FIGS. 9 to 26 are graphs of the results produced in accordance with the invention.

DESCRIPTION OF PREFERRED EMBODIMENT OF INVENTION

Figure 1:
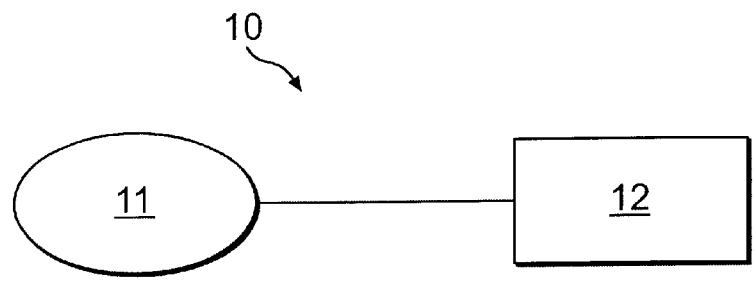
FIG. 1 is a schematic diagram illustrating the invention.
Figure 2:
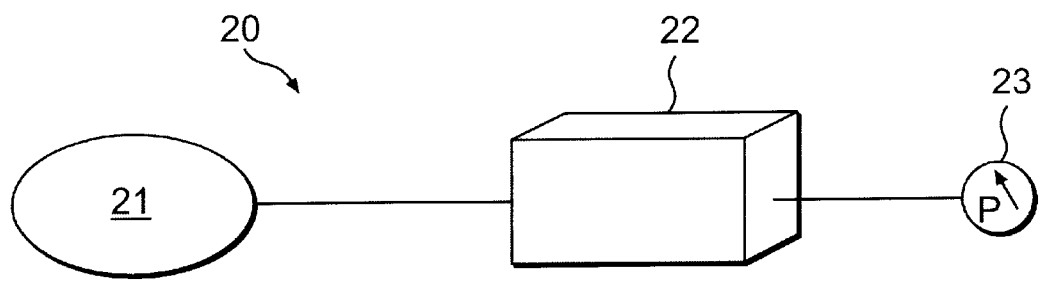
FIG. 2 schematically illustrates a first embodiment of the invention seen in FIG. 1.

As can be seen in FIG. 1, a hand grip assessment apparatus 10 consists of a pneumatic reservoir 11 in the form of a rubber bulb such as is used in a conventional blood pressure sphygmomanometer which refills by simple elastic recoil. Bulb 11 is therefore adapted to be repeatedly vented by a user. Apparatus 10 also includes measuring means 12 which measures parameters indicative of strength, work, work rate and speed of muscle contraction of a user in evacuating the reservoir means. FIG. 2 illustrates a first preferred embodiment of the invention in which measuring apparatus 20 includes a pneumatic bulb reservoir 21, a chamber 22 of constant volume and a manometer 23 for measuring the pressure within chamber 22.

Figure 3:
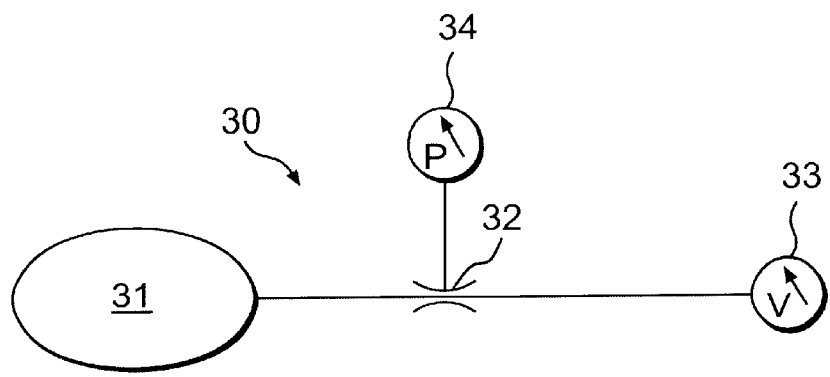
FIG. 3 schematically illustrates a second embodiment of the invention seen in FIG. 1.

Alternatively in another form of the invention as seen in FIG. 3 in which measuring apparatus 30 has a bulb reservoir 31, the constant volume chamber is replaced by a constant pressure valve 32 to which is coupled a measuring device 33 for measuring the volume of air which passes from the system through constant pressure valve 32. Manometer 34 measures the pressure at which valve 32 operates. The pressure at which valve 32 operates is selectively variable.

Figure 4:
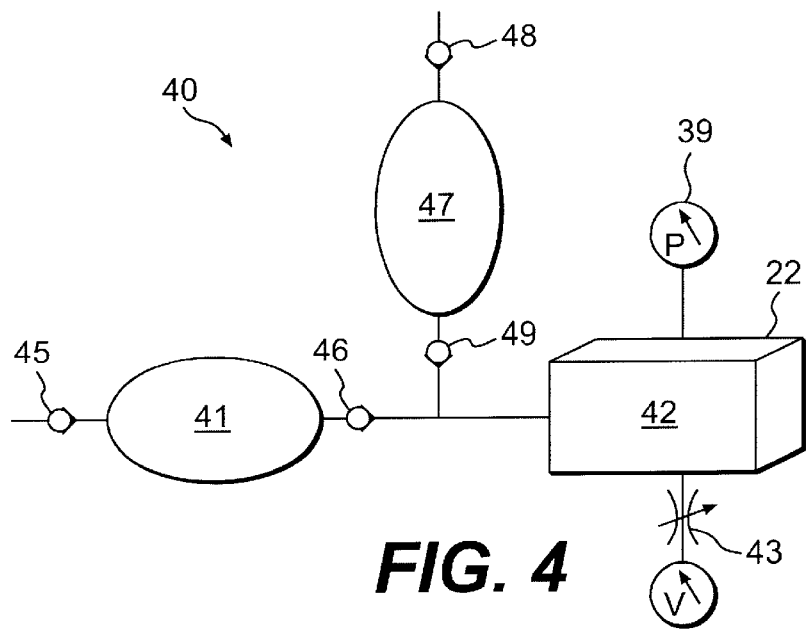
FIG. 4 schematically illustrates a third embodiment of the invention seen in FIG. 1.

FIG. 4 illustrates another form of the invention in which measuring apparatus 40 includes a pneumatic bulb reservoir 41 having non-return valves 45 and 46 connected on either side of the bulb reservoir to respectively prevent reflux of air from the bulb to atmosphere during operation and from the system to the bulb after operation. Constant volume chamber 42 is vented by a variable bleed valve 43. The rate of release is variable whereby when the user squeezes the bulb 41, the person conducting the test can vary the bleed rate of valve 43 to maintain a substantially constant pressure in constant volume chamber 42. The constant pressure within constant volume chamber 42 is read by means of manometer 39 and the volume of air pumped by the user at this pressure is measured by volumetric measuring device 44.

The analyst, ie the person conducted the tests, can vary the initial pressure within the constant volume chamber at which the tests commence. This is achieved by providing a second pneumatic bulb reservoir 47, or other pumping means, which is operated by the analyst. This arrangement can also be used with the embodiments illustrated in FIGS. 2 and 3.

It will be appreciated that a sphygmomanometer-type bulb reservoir has an elastic recoil pressure against which a user must work. This configuration requires unmeasured work to be performed each cycle against the elastic recoil of the bulb, thus introducing an error into the assessment by understating strength achieved and in the calculation of actual work performed. Where grip strength is greatly reduced, the inherent elastic recoil of the bulb requires significant strength to overcome and significant muscle work is performed in doing this. This unmeasured strength and work is a significant component of the actual strength required and work performed.

Figure 5:
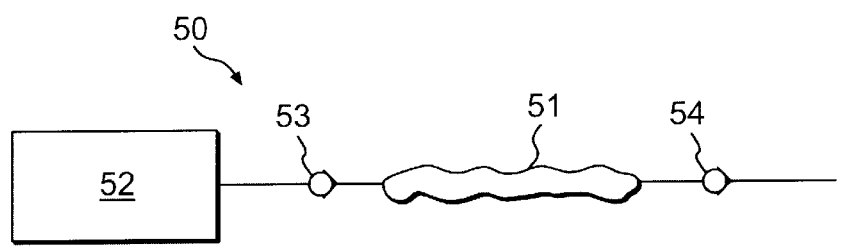
FIG. 5 illustrates an alternative embodiment of the pneumatic reservoir.

Accordingly, in another aspect of this invention illustrated in FIG. 5, this disadvantage is overcome by a collapsible bladder 51 which is reinflated by positive pressure source 52. Non-return valve 53 and 54 operate in a manner previously described. The pressure of the positive pressure source is deducted from that measured in the constant volume chamber or the operating pressure of the constant pressure valve.

Figure 6:
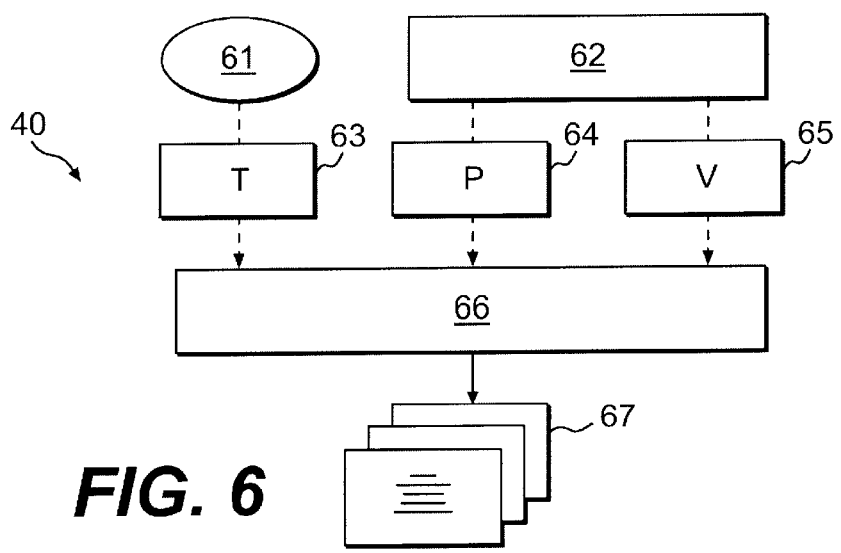
FIG. 6 schematically illustrates another embodiment of the invention.
Figure 8A:
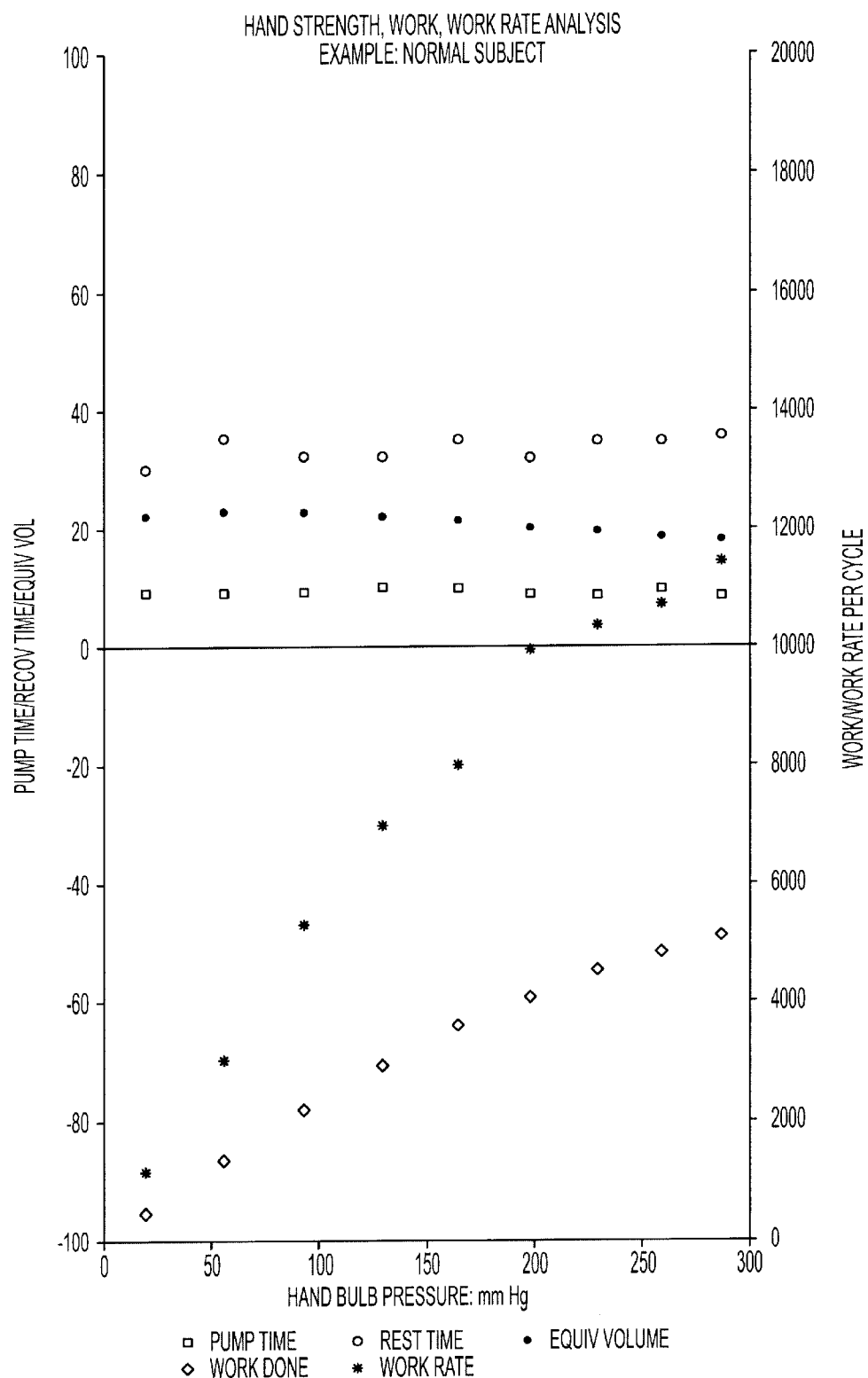
FIGS. 8A, 8B and 8C.
Figure 8B:
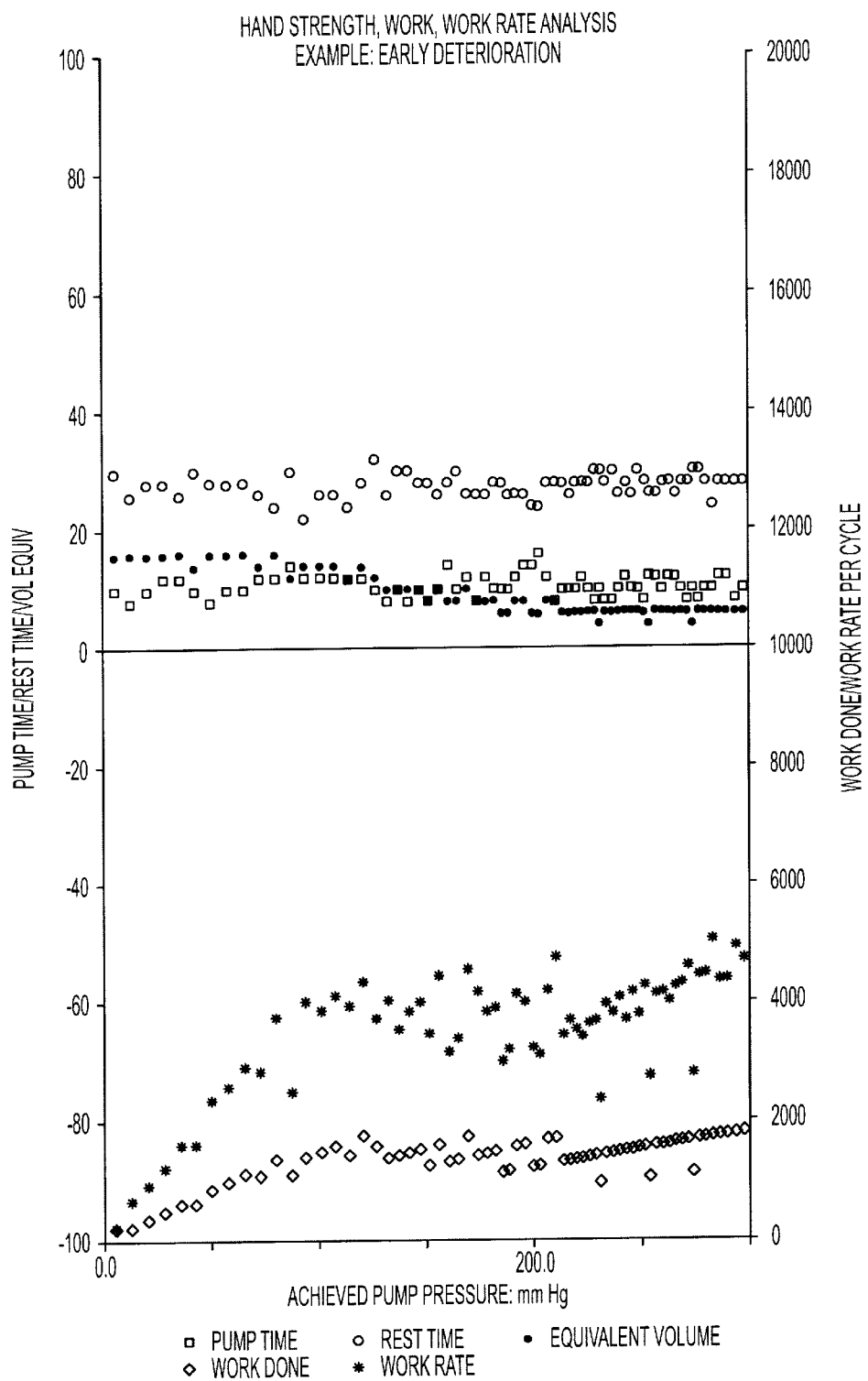
Figure 8C:
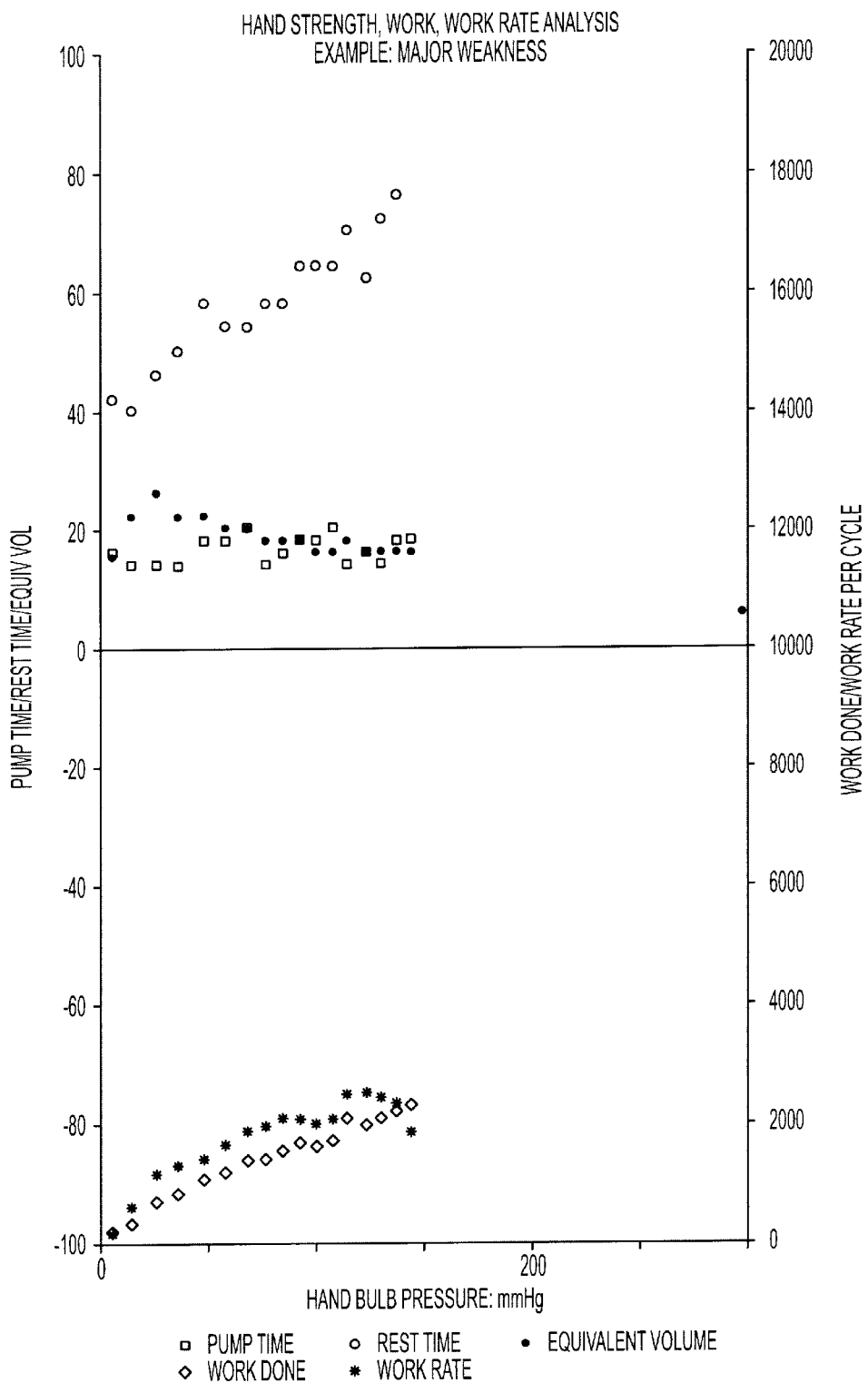
Figure 14:
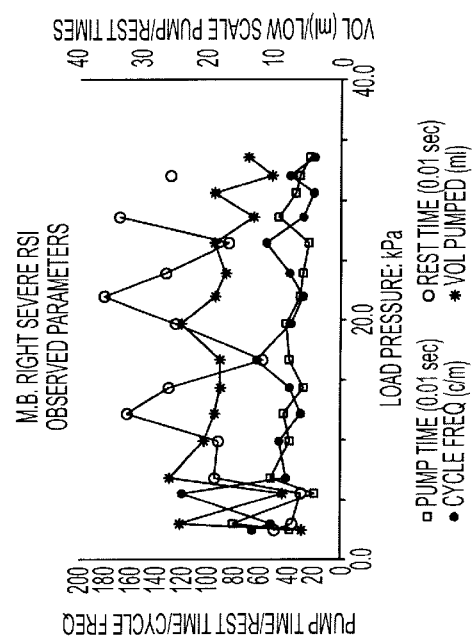
Figure 16:
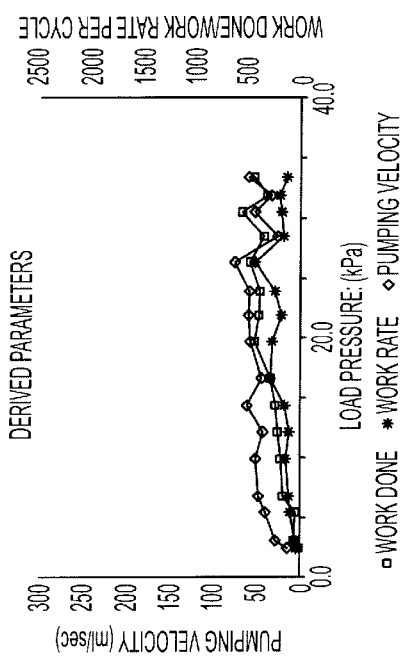
Figure 13:
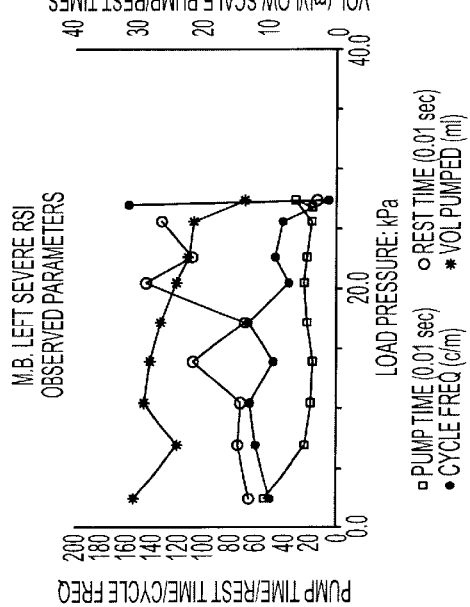
Figure 15:
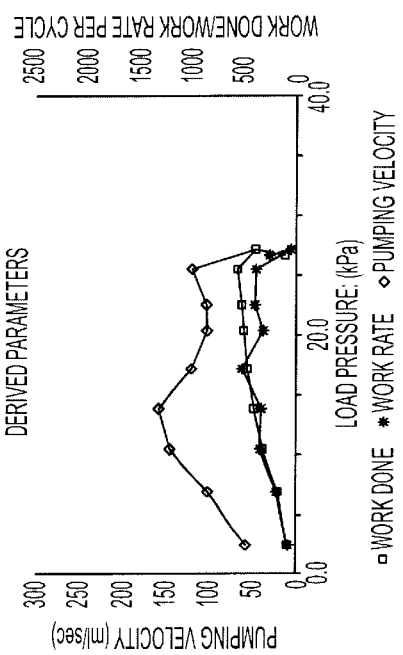
Figure 17:
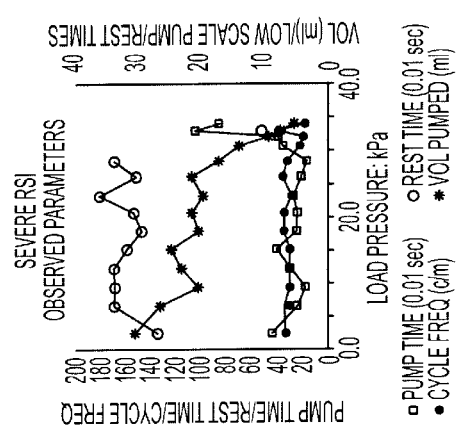
Figure 18:
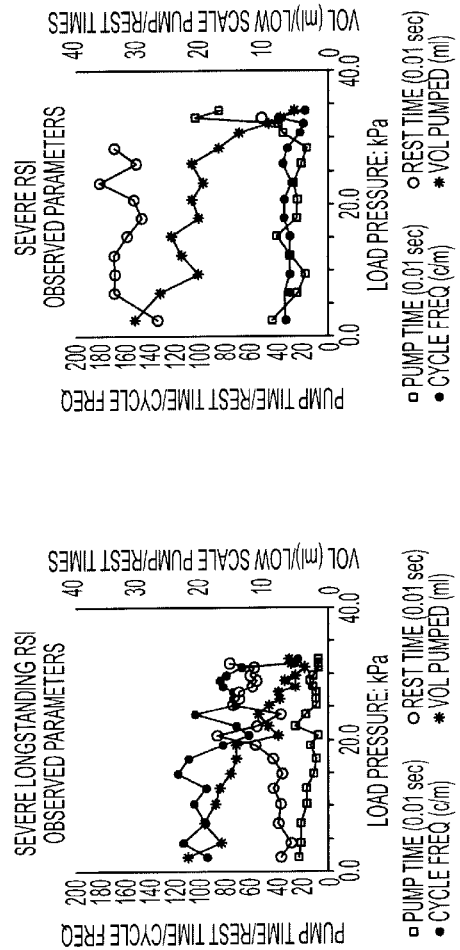
Figure 19:
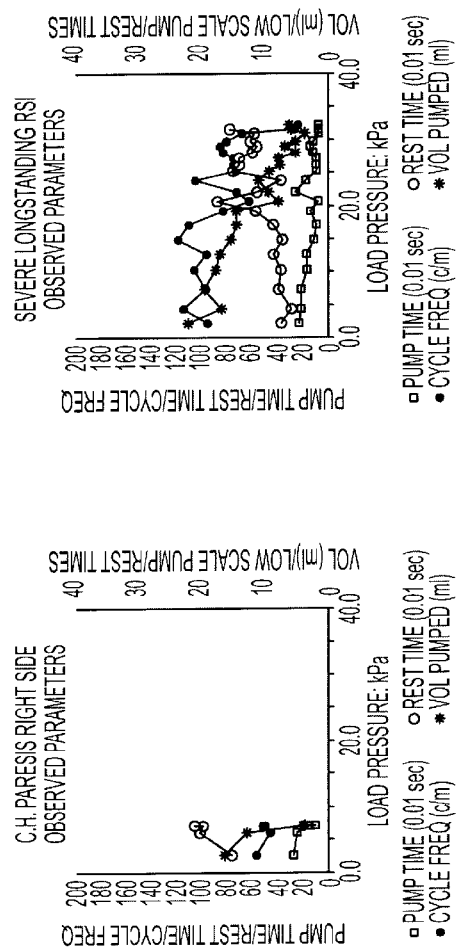
Figure 20:
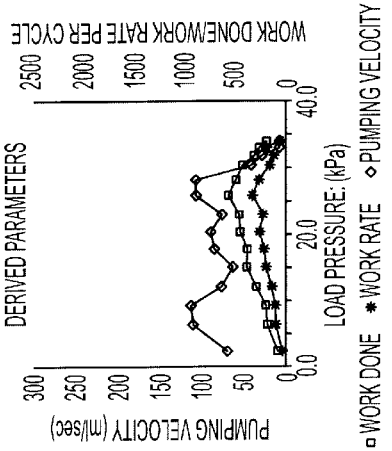
Figure 21:
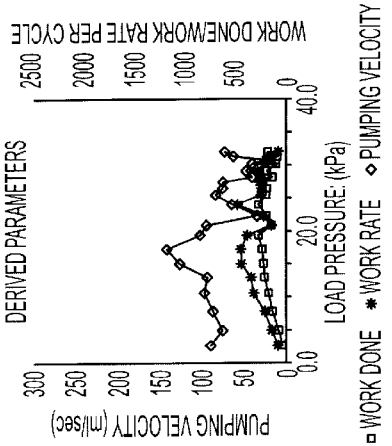
Figure 22:
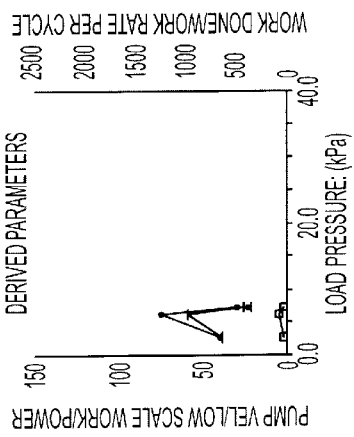

FIG. 6 illustrates a system 60 in which a pneumatic bulb reservoir 61 is repeatedly vented thereby varying the pressure and/or volume within an assembly 62. Timing means 63 are associated with bulb 61 and monitor the commencement and conclusion times of each operating cycle. Pressure measuring means 64 and volume measuring means 65 are associated with assembly 62 and measure pressure and volumetric changes associated therewith. The outputs of timing means 63, pressure measuring means 64 and volume measuring means 65 are connected with computation means 66 wherein calculations subsequently to be described are made. Calculating means 66 typically comprises a computer which produces an output 67 which is indicative of the strength, work, work rate and speed of muscle contraction performed by a user of the equipment with each pump cycle.

Although not illustrated in FIG. 6, it is to be realised that as well as measuring the pressure, control means that controls settings and actuates components of the apparatus, such as valves and pumps, between tests vary the volume of the constant volume chamber, and control the speed of metronome means that indicates to the subject the desired times of bulb reservoir evacuation. Such control means within the computation means can be managed by the analyst to set tests suitable for his or her intentions, or can administer a test process set up and programmed within the computation means, independent of and unknown to the analyst, to obtain a "double blind" assessment. Thus the control means can also control the venting valve (as for example via control from computer 66).

In this optional arrangement pressure measuring and controlling means 64 and volume measuring means 65 are associated with assembly 62 and measure and can control pressure and volumetric changes associated therewith. The outputs of timing means 63, pressure measuring and controlling means 64 and volume measuring means 65 are connected with computation means 66 wherein the calculations subsequently to be described are made.

The pressure setting of the constant pressure valve can conveniently be measured with a gauge or transducer sited between the exit valve of the bulb and the constant pressure valve. The pressure within the constant volume chamber can conveniently be measured within that chamber or elsewhere in the high pressure line.

The volume of air pumped can conveniently be measured either by a volumetric or integrated air flow measure attached to a priming mechanism that replenishes the gas in the bulb under low pressure, or by measuring the volume or the integrated air flow of air escaping from the constant pressure valve. Accuracy will be increased by minimising the dead-space between the bulb exit valve and the constant pressure valve. A constant volume chamber can also be incorporated into this configuration permitting a build up of pressure to a predetermined level, after which air injected by further pumping to vent the bulb will bleed from the chamber so maintaining constant pressure.

Measuring the duration of each pump cycle permits the calculation of the "rate of doing work" for each pump cycle. A good approximation can be obtained by observing the start and stop times of the increase in pressure measured in the constant volume chamber. More accurately, this information can be obtained by identifying the times of the opening and the closing of the bulb exit valve, or of the constant pressure valve.

The constant pressure valve embodiment allows the threshold pressure that permits flow of air to be varied, to allow study of the ability of the grip of the hand to do work against different pressures in the bulb. The configuration of this embodiment is the most analytical, as it permits continuing bulb evacuation cycles against a constant pressure at the will of the analyst, increases in the pressure also being able to be induced at the will of the analyst, at the times of his or her choice. Thus the strength and the endurance of the hand in grip work can be studied independently.

The configuration utilising a constant volume chamber without a constant pressure valve is a more simple and restricted system, as it utilises the volume of air pumped into the constant volume vessel by each pump cycle to increase the pressure in that vessel by a proportional amount. The volume of air pumped in is also directly proportional to the increase in pressure achieved in the pump cycle. This simplifies the system, as the accurate volume measure needed for the fixed pressure valve configuration can be dispensed with, the volume injected at each cycle being calculated directly from the increase in pressure. Useful results can be obtained from this system, with a variation of the pressure increase caused by injecting a constant volume of air being obtained by changing the volume of the chamber. Furthermore, the constant pressure valve can be simulated by using a variable flow release valve to obtain a constant rate of pumping using a metronome. Utilising different sized bulbs, injecting different aliquot volumes of air, provides for further variation. This further lessens the ability of a subject intent on fabricating disability and hiding that intent.

Use of the invention will now be described with reference to the two embodiments (a) using a constant volume chamber where there is incremental pressure increase without any loss through a valve outlet, and (b) using a configuration which achieves a steady pressure state (ie work against constant pressure) with air loss through either a constant pressure valve or a variable bleed valve. It is to be noted that although air is the gas commonly used in the apparatus, other gase can be effectively used.

In the first of these embodiments only pressure is measured and a mathematical calculation of a "volume equivalent pressure" is made. The user repeatedly pumps or squeezes the bulb to vent it and both the pressure of and time at the beginning and end of each evacuation or cycle is recorded. The process can continue until a predetermined pressure is reached or until the user is unable to continue pumping.

The system then calculates the average pressure of each cycle, the pressure increase achieved in each cycle and the equivalent volume of that pressure increase. The volume equivalent pressure is the product of the pressure increase and the volume of the chamber. With pressure stated in millimetres of mercury, the Rosendahl equivalent volume (REV) can be standardised to a one liter capacity chamber and then expressed arbitrarily as the REV (expressed in mils). For chambers of varying volume the equivalent volume per cycle is calculated by multiplying the pressure increase recorded in a cycle by the volume of the chamber (in liters). The work done during each cycle is the product of the average pressure during that cycle and the equivalent volume. Work can be expressed arbitrarily in RWUs (Rosendahl work units).

The duration of each cycle is determined from the time measurements and the rate of doing work in each cycle is calculated by dividing the work done in each cycle by the duration of the cycle (in seconds). The rate of doing work can be expressed arbitrarily in RPUs (Rosendahl power units).

In another embodiment the assessment instrument can be calibrated in SI units, pressure being measured in pascals, volume in liters, force in newtons, power in watts (or any convenient numerical derivative of these). For example the pressure is conveniently measured in kilopascals, the volume in milliliters. This provides a more ready comparison between assessments made using the pressure increase in the constant volume chamber and the flow through a pressure release valve.

In the embodiment that utilises a variable bleed or constant pressure vent valve, the analyst can control the valve so that the user establishes during successive cycles a substantially constant pressure in the high pressure line, which with the variable bleed valve will—and with the constant pressure vent valve may—include a constant pressure chamber. (To achieve the goal of constant pressure with the variable bleed valve there is a requirement that the subject maintain a constant pumping rate and eject the same volume of gas from the pneumatic reservoir in each pump cycle. There are no such requirements with the use of the constant pressure vent valve.) The system measures the pressure in the high pressure system, and the volume of air bled or vented from the variable bleed or constant pressure vent valve—or entered into the collapsible hand reservoir—over time, or per cycle time, or per pump duration and rest duration, or per aliquots of each, and the calculations are then made as described above. However, it will be appreciated that the volume measurements are real rather than of "volume equivalent pressure".

Sample measurements and calculations are illustrated in FIGS. 7A–7C, and FIGS. 8A–C show a graphic display of the results in which equivalent volume (including pump phase duration and recovery phase duration), work done and rate of doing work are plotted against an axis of increasing pressure.

The results were obtained from prototype apparatus, utilising a large sphygmomanometer dial, three bottles of volumes 600 ml, 1.25 liters and 2 liters respectively serving as a separate constant volume chambers, and a sphygmomanometer pump bulb adapted by inserting another back valve from another sphygmomanometer bulb into a length of rubber tubing, inserting this into the bulb end from which the variable flow release valve has been removed, and taping it securely into position, all these components being connected by lengths of rubber tubing. As the test is being performed the dial of the sphygmomanometer is videoed. Adjacent to the sphygmomanometer dial is a large LED display with timing circuits that displays three numeric LEDs, one cycling from zero to nine in one second intervals, the second cycling from zero to nine in one tenth second intervals, and the third cycling from zero to nine in one hundredth second intervals.

The data of time and pressure can then be conveniently read from selected frames of the video, a jog shuttle being used to find the start of the pump phase when the sphygmomanometer needle begins to move as further air is injected into the constant volume chamber, the start of the recovery phase being the time instant when the needle stops moving. The pressures are read directly off the dial.

For each cycle these parameters are entered into the data columns of the prepared spreadsheet.

The first row of the spreadsheet already has appropriate formulae prepared (the formulae are stated in spreadsheet form on the sample tabulation). These formulae are simply copied down for the number of pump cycles for which data has been abstracted from the video.

Seven specific parameters are graphed. The duration of the pump phase and the duration of the recovery phase of each pump cycle (in each 1/100 second) the inverse of the total cycle duration (the cycle frequency), the real volume, equivalent real volume (adjusted to unit constant volume vessel volume) or calculated volume equivalent pressure, the work performed, the rate of doing work, and the volumetric shortening velocity.

These are graphed as a "scattergram", the x co-ordinate being the average pressure achieved in each pump cycle as calculated by the spreadsheet.

The normal graph can be derived from some simple empirical observations. The normal adult male and female medical practitioner is able to pump to 300 mm Hg rapidly and without trouble when measure blood pressures. A rate of three pump cycles per second can be maintained to this pressure. The larger the volume of the constant volume chamber, the more pump cycles are required to reach the pressure of 300 mm Hg which is the standard cut-off point of pressure readings when taking blood pressure.

In the example illustrated a 600 mil chamber was utilised, the maximum pressure being obtained over ten pump cycles, nine of which are graphed. The duration of the pump phase was 8–10 one hundredths of a second, the duration of the recovery phase about 26–30 one hundredths of a second, the REV falling from about 20 mil to about 15 mil (as the pressure increases the "ejection fraction" diminishes). Nevertheless, the graph clearly demonstrates work performance in excess of 5000RWU at 300 mm Hg, and a power approaching 12000RPU at that pressure.

In the example described as "early deterioration", a 2 liter constant volume chamber was utilised. This provides for many more pump cycles (a total of 67 in all). The duration of the pump phase was unaltered from 8–10 seconds, and remained constant for the 67 pumps. The duration of the recovery phase was also maintained, the patient maintaining rhythm with a metronome set at 180 beats per minute however the REV was always less than 20 mil, and at a pressure of 125 mm Hg began to fade away, being less than 10 mil from 170 mm Hg onwards.

In attempting to maintain the rate set by the metronome, the patient only partially emptied the hand-bulb. With the reduction in the volume achieved the work performed never exceeded 200RWU, even though the full pressure of 300 mm Hg was obtained. Because the speed of pumping was maintained, the rate of doing work exceeded the numerical value of the work performed by a factor in excess of two, however a plateau is clearly seen developing at about 125 mm Hg pressure, and there is only one power reading in excess of 5000RPU.

The appearance of a dip and then a gradual increase from about 200 mm Hg reflects the encouragement given to the patient from that pressure.

In the example entitled "major weakness" the patient was unable to obtain a pressure greater than 150 mm Hg. The patient reported being fatigued and chose to stop despite encouragement. The duration of the pump phase remained relatively constant, but at a longer duration of close to 20 one hundredths of a second and the duration of the recovery phase increased from 40 one hundredths of a second to almost 80 one hundredths of a second over the duration of the test. The equivalent volume achieved was the maximum available at low pressures, but began to reduce gradually towards the end of the trial. The work performed was only marginally greater than 200RWU at 140 mm Hg pressure, while the rate of doing work began to decline on account of the increased recovery time at that pressure. The subject was not able to perform a pump cycle at any stage of the test in less than one half of a second, and by the time the trial was concluded at 140 mm Hg, the pump cycle required a full second to complete.

In comparison to the stage of "early deterioration", the state of "major weakness" is evident from a failure to achieve a pressure of 300 mm Hg, the reduction in speed of the pumping cycle from the very beginning to a rate no greater than 2 cycles per second, and a further reduction in that rate, the increase in time being found to occur in the recovery phase of the pump cycle.

While this, as it stands, could be seen to be the graph obtained from a person deliberately feigning weakness, further tests performed with different volumes, of the constant volume chamber, different sizes of hand-pump bulbs (especially where a limp flexible bladder is used to eliminate the error inherent in the resilient bulb) and, without the subject knowing it, the venting off of air about 100 mm Hg pressure should enable the tester to determine whether a person's complaint of major weakness, resulting in the observed inability to achieve a hand-bulb pressure greater than 140 mm Hg, and with a gradual increase in the duration of the recovery time, was consistently demonstrated in the various tests that can be performed.

The maximum power achieved by the repetitive exhaustion of the hand pump bulb is in principle independent of the mechanism and configuration of the mechanism used to measure it. Consequently, confirmatory evidence can be obtained that a subject has worked with maximal exertion in several tests by demonstrating equivalent values of maximum power by testing with differing volumes of the hand pump bulb or the constant volume chamber, or with differing speed of pumping.

The present invention can be utilised in the clinical testing of persons claiming significant loss of grip strength and the ability to perform work with the hand(s), in medical, occupational health, and pre-employment assessments.

As with blood pressure measurements, variability of results in one patient from test to test and from day to day is expected. However (as with blood pressure) certain norms will be able to be established as expected in a normal healthy adult male or female, and readings outside these expected norms will be a reason for closer study and further evaluation. Marked difference from these norms can be considered abnormal, and specific analysis and characterisation of those abnormalities can be made.

FIGS. 9 to 26 illustrate graphical presentations available with the present invention to assist in diagnostic evaluation.

As was defined previously, the present invention relates not only to a measurement assembly for and a method of measuring the strength of a user, but also relates to a method of treatment of patients having muscle weakness.

It is known that, persons having reduced muscle strength, whether caused by occupational overuse syndrome, cumulative trauma disorder, RSI or other cause, benefit physiologically from an exercise regime varying from mild in the case of severe disorder to moderate to heavy as the condition improves, especially where work is actually being performed. Although in the case of RSI there is debate as to what level of pain, if any, exercising should be taken, it is generally agreed that a patient should not work at or beyond a level that causes more than mild pain. The incremental or constant nature of the exercise afforded by the present invention allows the patient to thus effectively control the exercise regime in this regard.

Moreover the invention has an important psychological benefit. Persons suffering from occupational overuse syndrome, cumulative trauma disorder or RSI frequently become depressed not only because of slow recovery which may take a number of years, but also because severe bouts of pain can frequently re-occur which can mask the fact that there may have been a significant improvement in the disability threshold. This depression has a direct adverse impact on the physical condition which is made worse by tension.

In this regard the present invention serves a most useful purpose in displaying to the patient empirical evidence that progress is being maintained in spite of reoccurrence of pain even at a level as severe as previously.

In use in this aspect of the invention, the repeated evacuation of the bulb at an appropriate set pressure provides an exercise regime at a level conditional upon the patient's condition in that the patient works to his or her level of comfort, pain and disability. As the threshold level of the condition improves the exercise regime strengthens and importantly, the patient receives positive feedback by way of seeing the graphically displayed results which compare favourably with the results at an earlier period of the condition when the threshold level was worse. This encourages the patient at times when pain regressions mask the fact of overall and continuing improvement and lessen the potential for the patient to become depressed.

It will be appreciated that the apparatus and method of the present invention pneumatically measures grip strength, grip work and rate of grip work per pneumatic pump cycle. Grip work is measured by computing the product of pressure and volume and uses that computation of grip work, divided by the time taken for each work cycle, to compute the rate of doing grip work per cycle. By calculating the "equivalent volume" from the pressure excursion obtained in each single pump cycle there is no requirement for volume measurement in the calculation of grip work when using the constant volume chamber. Simulation of constant pressure testing at constant pumping rates is possible when using a fixed volume chamber by the provision of a variable aperture flow release valve, ie variable bleed valve.

As well as strength, work, and work-rate parameters, the present invention provides a measure of muscle shortening and relengthening velocity, both as an average for each pump cycle, and plotted at short time intervals during any specific pump duration and recovery duration. The muscle shortening information (including both an average shortening velocity for each pump cycle and an "instantaneous" shortening velocity plotted at short time intervals for a given pump cycle) can be derived from the total increase in pressure occurring in a pump duration, and by measuring the increments in pressure occurring over short time periods (as for example 10 millisecond intervals) during a pump duration.

This is achieved by setting a low volume for the constant volume chamber to thereby provide for large pressure increments in each pump cycle.

The average relengthening velocity and the incremental relengthening velocity are indicated by the average flow rate and the incremental flow rate of air from the source of positive pressure used to re-inflate a limp collapsible hand pump bladder in the recovery duration of a pump cycle.

This provides a valuable measure of the rapidity with which the hand can return to the start position to begin a new pump cycle.

The testing device of the present invention can measure pressures substantially greater than that available with a sphygmomanometer, and the testing process can be continued until the maximum pressure is reached (ie the person can no longer force air from the hand pump bulb into the constant volume chamber), or the subject stops on account of the severity of the pain induced by the attempt.

In adult females pressures up to 100 kilopascals can commonly be attained. In males maximum pressures from 80 to 150 kilopascals can be attained. The upper levels of pressure attained by each gender is achieved by persons who are well-muscled and in training.

The extension of the test into the higher pressure range provides for a completion of the relevant parameters.

It is observed that in the normal person:
(a) The pump duration tends to continue at the same value until the very end of the attempt when it increases substantially.
(b) If a person is instructed to pump as rapidly as they can, and the collapsible reservoir does not limit the speed of the recovery duration, recovery duration initially is constant. However, once the pressure load at maximum power output is attained, the recovery duration tends to increase, slowly at first, then more rapidly.
(c) In the embodiments illustrated the volume injected reduces slowly from the beginning but starts to fade rapidly once maximal power has been achieved.
(d) The work achieved per cycle peaks at the point where the person can only just continue to fully empty the bulb. After that stage as the capacity to empty the bulb diminishes the work performed also diminishes.
(e) The power output peaks at a point related to the peak of work performed per pump cycle, but also starts to diminish as the total cycle duration lengthens.
(f) The shortening velocity starts at a high level, reduces slowly as the load increases, and reduces rapidly after maximal power is achieved.

Thus a relatively standard set of curves can be provided for each test which can be interpreted as normal or abnormal depending on the specific values achieved with each parameter.

The present invention furthermore allows a series of tests to be performed for each hand, by changing the variables of volume of the hand pump bulb, volume of the constant volume chamber, speed of pumping, or varying from a constant volume to a set pressure technique.

For clinical purposes the variation of the parameters will be controlled by the testing physician. However in an alternative embodiment not illustrated, the present invention allows for non-clinical testing which is common for medico-legal work or where a less skilled person is conducting the test. In this arrangement variation of the parameters for a sequence of tests can be controlled by a program within the connected computer. This option can also of course be utilised for clinical testing and with this embodiment, not even the person who is conducting the test may be able to give, by voluntary or involuntary cues, any indication of the settings of the test process controlled from within the computer.

The invention has a number of advantages over known methods and apparatus for assessing strength. These include the following:

The present invention can assess muscular strength, endurance, work performed, power generated, the speed of contraction of the muscle system, disability of muscle action, and it is believed susceptibility to the onset of upper limb disability (and pain) precipitated by repetitive hand grasp or finger action.

Attempted maximal isometric grasp using known equipment typically precipitates severe neuropathic pain and decreased grip strength in persons with RSI which pain can then last for minutes, hours or days. Persons claiming this disorder do not like attempting this test on known equipment, and the results obtained using known equipment are commonly disputed. The incremental approach of the present invention substantially lessens the risk of precipitating these adverse effects, nevertheless providing meaningful and useful results.

The present invention provides the means for the hand to perform formal incremental work by repeatedly squeezing a bulb to partially empty it of air, the air being forced into a constant volume chamber or through a constant pressure valve. The work done in each cycle is the product of the volume pumped and pressure against which the air is forced, either through the constant pressure valve or present in the constant volume chamber.

The present invention in one embodiment allows for precise measurement of grip strength by the use of the adjustable constant pressure relief valve. A target level of pressure is set and the ability of the hand to meet this target level is assessed. The target level can be incrementally increased or decreased at will by the analyst. In this embodiment the means to test grip strength and grip endurance are independent of each other.

The present invention allows for the performance and testing of both repetitive constant work load and incremental work load.

Testing of grip strength, grip work and rate of grip work with the present invention gives results which are accurate at low values.

The present invention provides a number of independent ways to assess the possibility of a subject attempting to feign disability by perversely simulating maximal effort. These include (1) control and variation of threshold valve pressure which is unknown to the subject,
(2) control and variation of the volume of the "fixed" volume version which is unknown to the subject,
(3) the substitution of different volume hand bulbs, so varying the maximum injection volume and the effective grasp leverage the hand can apply in pump injection,
(4) the variation of more than one of these parameters between tests, and
(5) by assessing the power output of the hand at different set cycle rates, by asking the subject to as fully possible empty the hand pump bulb or collapsible reservoir, at the same time maintaining the pumping rate set by a metronome device. When reasonable pumping rates are set, and there is no evidence of primary muscular incoordination, the maximum power output developed and demonstrated in each test should be reasonably similar, and as the pumping rate is increased, the maximum power output should be achieved at a lower pressure load.

It will of course be realised that whilst the above has been given by way of an illustrative example of this invention, all such and other modifications and variations hereto, as would be apparent to persons skilled in the art, are deemed to fall within the broad scope and ambit of this invention as is herein set forth.

Thus for example, the apparatus of the present invention could also include computational means for conducting a test sequence independent of an analyst to thereby obtain a demonstrably objective and unbiased result. The fluid in the reservoir means can be a liquid as well as a gas. The graphical presentation obtained by the computational means could be of contraction time, recovery time, cycle frequency and pump volume (or volume equivalent pressure) plotted against load (average cycle pressure). The graphical presentation derived by the computational means could also be in respect of work performed, power achieved and volumetric shortening velocity plotted against load (average cycle pressure). Furthermore, the graphical presentation of the specific parameters calculated or derived by the computational means, can be presented either as an average for each complete pump cycle, or as interval measures within a cycle for brief (almost instantaneous) aliquots of time.

It will also be appreciated that because exercise apparatus and sports training equipment is often operated hydraulically, the apparatus of the present invention may be incorporated therein, with either gas or liquid fluid in the reservoir, whereby the parameters of work performed and power generated can be calculated and displayed for each action cycle. The invention may be incorporated in the exercise apparatus and sports training equipment either initially upon manufacture or by retrofitting to existing apparatus and equipment.

The claims defining the invention are as follows:

1. An apparatus for assessing a user's strength, said apparatus comprising:
    a deformable reservoir for venting by the user by deformation thereof during a testing sequence of reported ventings;
    a constant volume chamber in fluid communication with said deformable reservoir to receive fluid vented from said deformable reservoir,
    measuring means operatively coupled to said constant volume chamber for measuring fluid parameters indicative of at least one of strength, work, work rate and speed of muscle contraction of the user associated with evacuation of said reservoir into said constant volume chamber during the testing sequence, and
    display means operatively connected to said measuring means for displaying said indicative parameters;
    wherein said measuring means includes means for measuring the pressure in said constant volume chamber.

2. An apparatus as claimed in claim 1, wherein said deformable reservoir is pneumatic.

3. An apparatus as claimed in claim 2, wherein said pneumatic reservoir is a resilient bladder adapted to resile from a deflated configuration after evacuation to an inflated configuration for re-evacuation.

4. An apparatus as claimed in claim 2, wherein said pneumatic reservoir is a limp collapsible bladder, and the apparatus comprises a source of positive pressure to re-inflate said bladder from a deflated configuration after evacuation to an inflated configuration for re-evacuation.

5. An apparatus as claimed in claim 4, further comprising one or more of: means for controlling the volume of said constant volume chamber, means for controlling the initial pressure of said constant volume chamber, and means for controlling the pressure of a positive pressure source for supply to a limp collapsible bladder.

6. An apparatus as claimed in claim 1, wherein the volume of said constant volume chamber is selectively variable.

7. An apparatus as claimed in claim 1, wherein said measuring means comprises means for measuring the time at the beginning and end of each evacuation and the duration of each evacuation and the interval between evacuations.

8. An apparatus as claimed in claim 7, wherein said measuring means comprises means for calculating parameters indicative of strength, work, work rate and speed of muscle contraction of the user.

9. An apparatus as claimed in claim 1, wherein said constant volume chamber comprises a variable bleed valve to selectively vary the pressure in the constant volume chamber such that the pressure therein remains substantially constant after each successive evacuation thereof.

10. An apparatus as claimed in claim 9, wherein said measuring means comprises:
    means for measuring the pressure at which said constant volume chamber operates; and
    means for controlling the constant pressure within said constant volume chamber or means for varying the setting of said variable bleed valve.

11. An apparatus as claimed in claim 1, said apparatus further comprising means for generating pressure to selectively control the initial pressure in said constant volume chamber.

12. An apparatus as claimed in claim 1, said apparatus comprising non-return valves located at the inlet and outlet of said pneumatic reservoir, said non-return valves respectively preventing reflux of a gas from the pneumatic reservoir when operated by a user and preventing reflux of gas from the constant volume chamber to the reservoir after operation of the reservoir by the user.

13. An apparatus as claimed in claim 1, said apparatus comprising means for indicating time intervals to a user.

14. An apparatus as claimed in claim 13, wherein said time intervals are timings of muscle contraction.

15. An apparatus as claimed in claim 1, said apparatus further comprising computational means for conducting a test sequence independent of an analyst to thereby obtain a demonstrably objective and unbiased result;

wherein the fluid in the reservoir is a liquid and not a gas;

wherein the graphical presentation obtained by the computational means is of contraction time, recovery time, cycle frequency and one of pump volume and volume equivalent pressure plotted against load;

wherein the graphical presentation derived by the computational means is in respect of work performed, power achieved and volumetric shortening velocity plotted against load;

wherein the graphical presentation of the specific parameters calculated or derived by the computational means, is presented either as an average for each complete pump cycle, or as interval measures within a cycle for brief aliquots of time;

and wherein the apparatus is incorporated in hydraulically operated exercise apparatus and sports training equipment either initially upon manufacture or by retrofitting to existing apparatus and equipment, with either gas or liquid fluid in the reservoir, whereby the parameters of work performed and power generated can be calculated and displayed for each action cycle.

16. An apparatus for assessing a user's strength, said apparatus comprising:

a deformable reservoir for venting by the user by deformation thereof during a testing sequence of repeated ventings;

a constant pressure valve operable at a predetermined pressure and connected to said deformable reservoir to thereby define the pressure to be exceeded before said reservoir can be vented;

measuring means operatively connected to said constant pressure valve for measuring parameters indicative of at least one of strength, work, work rare and speed of muscle contraction of the user associated with evacuation of said reservoir during the testing sequence, and display means operatively connected to said measuring means for displaying said indicative parameters;

wherein said measuring means includes means for measuring the volume expelled from said constant pressure valve.

17. An apparatus as claimed in claim 16, wherein the operating pressure of said constant pressure valve is selectively variable.

18. An apparatus as claimed in claim 16, wherein said measuring means comprises means for measuring the pressure at which said constant pressure valve operates.

19. An apparatus as claimed in claim 16, wherein said deformable reservoir is pneumatic.

20. An apparatus as claimed in claim 19, wherein said pneumatic reservoir is a resilient bladder adapted to resile from a deflated configuration after evacuation to an inflated configuration for re-evacuation.

21. An apparatus as claimed in claim 19, wherein said pneumatic reservoir is a limp collapsible bladder, and the apparatus comprises a source of positive pressure to re-inflate said bladder from a deflated configuration after evacuation to an inflated configuration for re-evacuation.

22. An apparatus as claimed in claim 16, wherein said measuring means comprises means for measuring the time at the beginning and end of each evacuation and the duration of each evacuation and the interval between evacuations.

23. An apparatus as claimed 22, wherein said measuring means comprises means calculating parameters indicative of strength, work, work rate and speed of muscle contraction of the user.

24. An apparatus as claimed in claim 16, said apparatus comprising non-return valves located at the inlet and outlet of said pneumatic reservoir, said non-return valves respectively preventing reflux of a gas from the pneumatic reservoir when operated by a user and preventing reflux of gas from the constant volume chamber to the reservoir after operation of the reservoir by the user.

25. An apparatus as claimed in claim 16, said apparatus comprising means for indicating time intervals to a user.

26. An apparatus as claimed in claim 25, wherein said time intervals are timings of muscle contraction.

27. A method of assessing and treating muscle weakness, comprising:

causing a patient to repeatedly vent fluid from a deformable reservoir during a testing sequence of repeated ventings;

selectively maintaining at least some of the vented fluid at substantially constant conditions as the patient repeatedly vents the fluid from the deformable reservoir;

allowing at least some of the vented fluid to escape the substantially constant conditions; and measuring parameters of the vented fluid allowed to escape the substantially constant conditions, said parameters being indicative of at least one muscle performance parameter selected from the group consisting of strength, work, work rate and speed of muscle contraction.

28. The method of claim 27, wherein the fluid is maintained at a substantially constant pressure with a constant volume chamber.

29. The method of claim 27, wherein the escape of the fluid from the substantially constant conditions is controlled by a constant pressure valve.

30. The method of claim 27, further comprising displaying to the patient the measured parameters.

31. The method of claim 27, comprising comprising the measured parameters with previously measured parameters from the patient so as to determine a degree of clinical improvement of the patient.

32. The method of claim 27, further comprising comparing the measured parameters with a norm.

* * * * *